(12) United States Patent
Burton et al.

(10) Patent No.: US 7,641,640 B2
(45) Date of Patent: Jan. 5, 2010

(54) MEDICAL VACUUM ASPIRATION DEVICE

(75) Inventors: Nadine Ferdman Burton, Durham, NC (US); Elizabeth Shires Maguire, Chapel Hill, NC (US); Ann Hamilton Leonard, Chapel Hill, NC (US); Robin Lyn Banker, Cary, NC (US); Michael Patrick Rouleau, Cary, NC (US); Paul D. Blumenthal, Baltimore, MD (US); Terence Stanely Kominski, Cary, NC (US)

(73) Assignee: IPAS, Chapel Hill, NC (US)

( * ) Notice: Subject to any disclaimer, the term of this patent is extended or adjusted under 35 U.S.C. 154(b) by 72 days.

(21) Appl. No.: 11/717,727

(22) Filed: Mar. 14, 2007

(65) Prior Publication Data

US 2007/0161965 A1    Jul. 12, 2007

Related U.S. Application Data

(63) Continuation of application No. 10/712,265, filed on Nov. 14, 2003.

(51) Int. Cl.
*A61M 1/00* (2006.01)
(52) U.S. Cl. .................. 604/319; 604/250; 600/565
(58) Field of Classification Search .......... 604/319, 604/321, 326, 131, 187, 6.12, 121, 232, 164.08, 604/263, 248, 250, 30–35, 143; 433/91; 137/205; 600/578, 579, 565; 221/105; 436/54
See application file for complete search history.

(56) References Cited

U.S. PATENT DOCUMENTS

| | | | | |
|---|---|---|---|---|
| 2,709,542 A | * | 5/1955 | Eller et al. | 222/209 |
| 3,610,242 A | * | 10/1971 | Sheridan et al. | 604/119 |
| 3,747,812 A | * | 7/1973 | Karman et al. | 222/387 |
| 3,994,294 A | * | 11/1976 | Knute | 604/152 |
| 4,366,816 A | | 1/1983 | Bayard et al. | 604/403 |

(Continued)

FOREIGN PATENT DOCUMENTS

EP    0 150 666 A1    8/1985

(Continued)

OTHER PUBLICATIONS

"IPAS Double-Valve Aspirator", IPAS, Inc., http://www.ipas.org/english/products/mva/double_valve_aspirator.asp, pp. 1-3.

(Continued)

*Primary Examiner*—Tatyana Zalukaeva
*Assistant Examiner*—Paula L Craig
(74) *Attorney, Agent, or Firm*—Morgan Lewis & Bockius LLP

(57) ABSTRACT

A medical vacuum aspiration device includes an aspiration cylinder and a valve. The valve includes a removable fluid conduit, a valve housing having at least first and second housing portions, means for removably attaching the first housing portion to the second housing portion, and an actuator. The removable fluid conduit has a first end for attaching to a cannula and a second end for attaching to the aspiration cylinder. The first and second housing portions may define a cavity for removably holding at least a portion of the fluid conduit. The actuator is coupled to the valve housing and selectively compresses a portion of the fluid conduit to open and close a fluid path defined by the fluid conduit.

21 Claims, 8 Drawing Sheets

U.S. PATENT DOCUMENTS

| | | | | |
|---|---|---|---|---|
| 4,425,116 A * | 1/1984 | Bilstad et al. | | 604/34 |
| 4,576,593 A | 3/1986 | Mommer | | |
| 4,813,931 A | 3/1989 | Hauze | | 604/540 |
| 4,909,792 A | 3/1990 | Norelli | | 604/192 |
| 5,098,416 A | 3/1992 | Imonti | | 604/319 |
| 5,102,394 A | 4/1992 | Lasaitis et al. | | 604/164.08 |
| 5,115,816 A | 5/1992 | Lee | | 600/562 |
| 5,186,714 A | 2/1993 | Boudreault et al. | | 604/21 |
| 5,195,959 A * | 3/1993 | Smith | | 604/34 |
| 5,219,333 A | 6/1993 | Sagstetter et al. | | 604/110 |
| 5,254,083 A * | 10/1993 | Gentelia et al. | | 604/35 |
| 5,300,043 A | 4/1994 | Devlin et al. | | 604/250 |
| 5,496,270 A * | 3/1996 | Nettekoven | | 604/30 |
| 5,518,004 A | 5/1996 | Schraga | | 600/473 |
| 5,591,134 A | 1/1997 | Shu | | 604/192 |
| RE35,539 E | 6/1997 | Bonaldo | | 128/763 |
| 5,713,914 A | 2/1998 | Lee | | |
| 5,749,859 A | 5/1998 | Powell | | 604/167.03 |
| 6,149,622 A * | 11/2000 | Marie | | 604/43 |
| 6,364,853 B1 | 4/2002 | French et al. | | |
| 6,506,165 B1 * | 1/2003 | Sweeney | | 600/562 |
| 6,632,201 B1 | 10/2003 | Mathias et al. | | 604/263 |
| 6,719,715 B2 * | 4/2004 | Newman et al. | | 604/6.08 |
| 2002/0029006 A1 * | 3/2002 | Turturro et al. | | 600/562 |
| 2005/0107757 A1 * | 5/2005 | Burton et al. | | 604/319 |

FOREIGN PATENT DOCUMENTS

| | | |
|---|---|---|
| EP | 0 836 858 A1 | 4/1998 |
| EP | 0 948 971 A1 | 10/1999 |
| FR | 1077898 | 11/1954 |

OTHER PUBLICATIONS

"*IPAS Single Valve Aspirator*", IPAS, Inc. http://www.ipas.org/english/products/mva/single_valve_aspirator.asp, pp. 1-2.

* cited by examiner

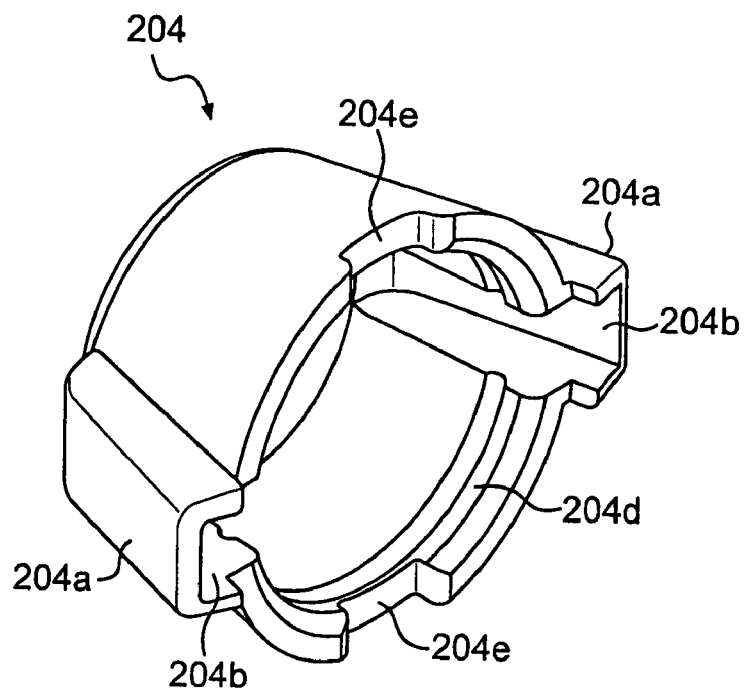
FIG. 9
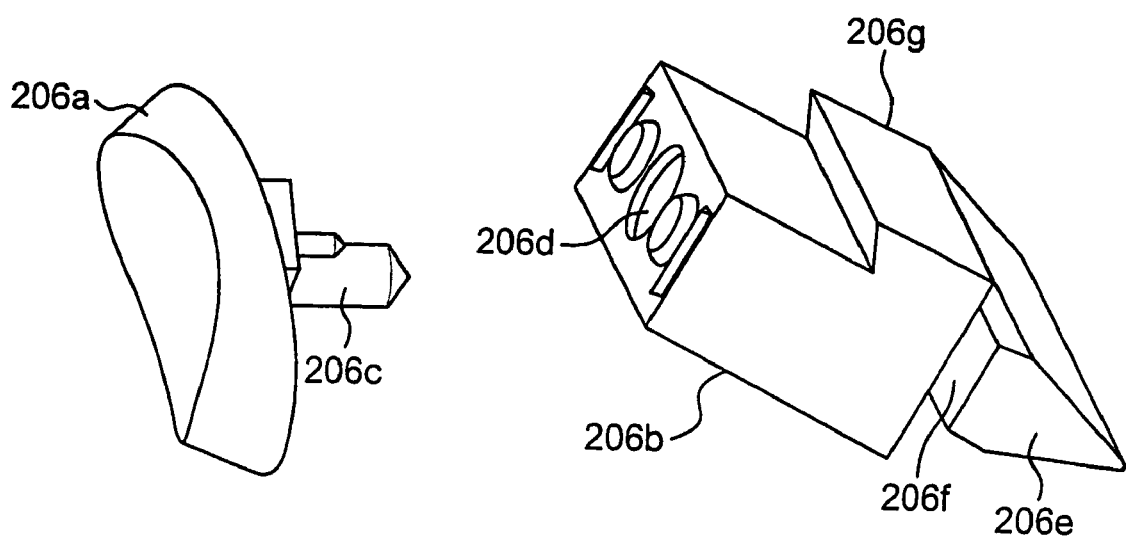
FIG. 10
FIG. 11

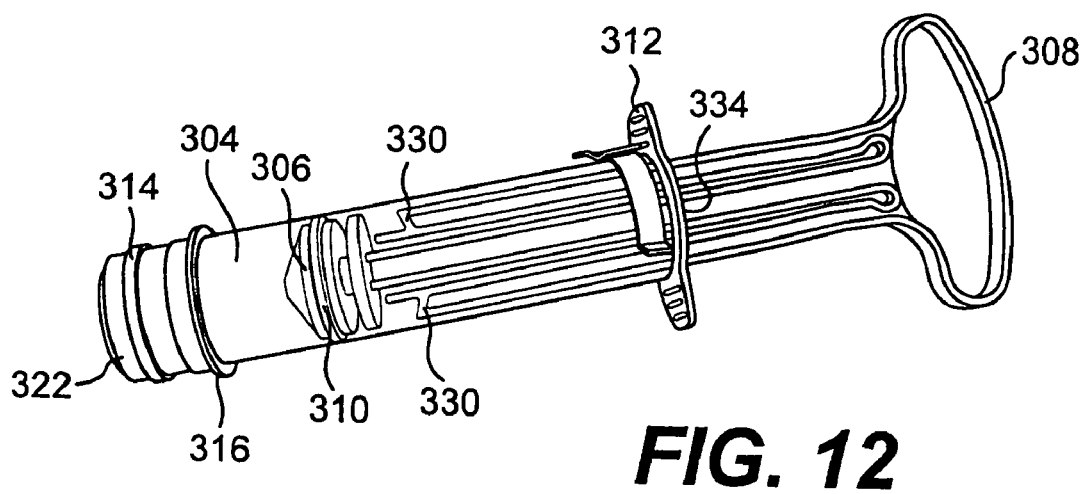
FIG. 12
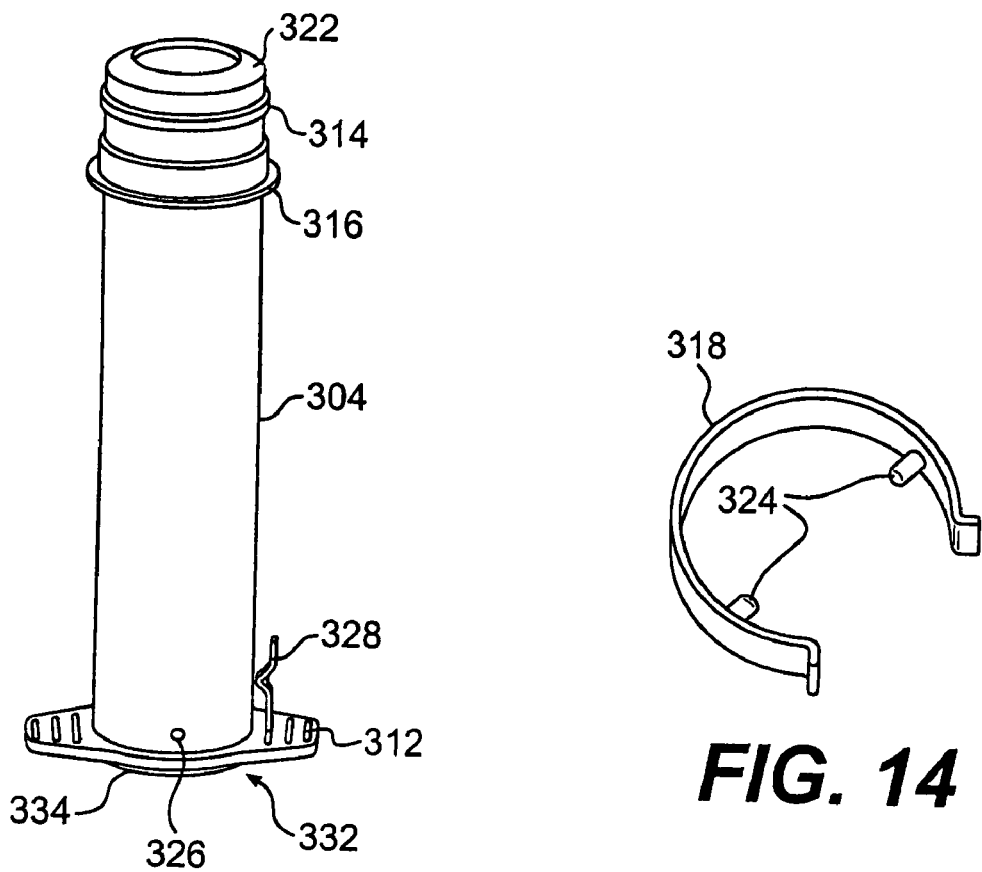
FIG. 13
FIG. 14

MEDICAL VACUUM ASPIRATION DEVICE

This application is a continuation of U.S. application Ser. No. 10/712,265, filed on Nov. 14, 2003, which is hereby incorporated in its entirety by reference.

BACKGROUND OF THE INVENTION

The present invention relates to a medical vacuum aspiration device (MVA). In general, it is more economical for MVAs to be used multiple times before they are disposed. Between uses, the MVA should be sterilized and/or disinfected. However, the materials chosen for the components of the MVA may be susceptible to degradation and/or damage by certain sterilization procedures and disinfectants. For example, latex components of the MVA can oxidize in an autoclave and certain plastic components can melt in an autoclave or degrade in the presence of chemical disinfectants.

Some MVAs are difficult to adequately clean and sterilize because they cannot be disassembled sufficiently. Other MVAs can include multiple parts that can be disassembled for sterilizing and disinfecting. However, the parts are easily misplaced or lost when disassembled. Further, a plurality of interfaces must be provided between each of the parts in order to connect the parts together and provide proper sealing to maintain the vacuum in the fluid path extending through the MVA. The plurality of interfaces can harbor tissue and fluid that can be difficult to remove during the sterilizing and disinfecting procedures. There remains a need for an MVA that is economical, safe, effective, and easily cleaned and sterilized.

SUMMARY OF THE INVENTION

There is provided an MVA that is easily cleaned and sterilized.

There is provided an MVA that is less susceptible to material degradation.

There is provided an MVA that can be used safely.

There is provided an MVA that can be made and used economically.

There is provided an MVA that can maintain the vacuum seal along the entire fluid path of the MVA.

There is provided an MVA that can be easy and comfortable to grasp and operate by a user.

There is also provided a medical vacuum aspiration device including an aspiration cylinder and a valve. The valve includes a removable fluid conduit, a valve housing having at least first and second housing portions, means for removably attaching the first housing portion to the second housing portion, and an actuator. The removable fluid conduit can have a first end for attaching to a cannula and a second end for attaching to the aspiration cylinder. The first and second housing portions may define a cavity for removably holding at least a portion of the fluid conduit. The actuator can be coupled to the valve housing and selectively compresses a portion of the fluid conduit to open and close a fluid path defined by the fluid conduit.

There is yet also provided a medical vacuum aspiration device including an aspiration cylinder and a valve adapted for fluid communication with the aspiration cylinder. The valve includes first and second housing portions, a releasable connector, a fluid conduit and at least one conduit clamp. The first and second housing portions each include inner and outer walls. The releasable connector joins the first housing portion to the second housing portion such that the first housing portion and the second housing can cooperate to define a housing having first and second open ends and a cavity defined by the inner walls and extending between the first and second open ends. The fluid conduit can be retained in the cavity when the first and second housing portions are joined by the releasable connector. The fluid conduit can be exposed for removal from the cavity when the releasable connector is released. The fluid conduit can include a flexible conduit portion. The at least one conduit clamp can be movably mounted on one of the housing portions and engagable with the flexible conduit portion to compress the conduit portion.

BRIEF DESCRIPTION OF THE DRAWINGS

The accompanying drawings, which are incorporated herein and constitute part of this specification, illustrate an embodiment of the invention, and, together with the general description given above and the detailed description given below, serve to explain the features of the invention.

FIG. 9 is a perspective view of a cap according to FIG. 2.

FIG. 10 is a perspective view of a button face of a button for opening and closing the valve according to the FIG. 2.

FIG. 11 is a perspective view of a clamp stem of a button for opening and closing the valve according to the FIG. 2.

FIG. 12 is a perspective view of the aspiration cylinder of the medical vacuum aspiration device according to FIG. 1.

FIG. 13 is a perspective view of a collection tube of the aspiration cylinder according to FIG. 12.

FIG. 14 is a perspective view of a plunger stop of the aspiration cylinder according to FIG. 12.

DETAILED DESCRIPTION OF THE PREFERRED EMBODIMENT

Figure 1:
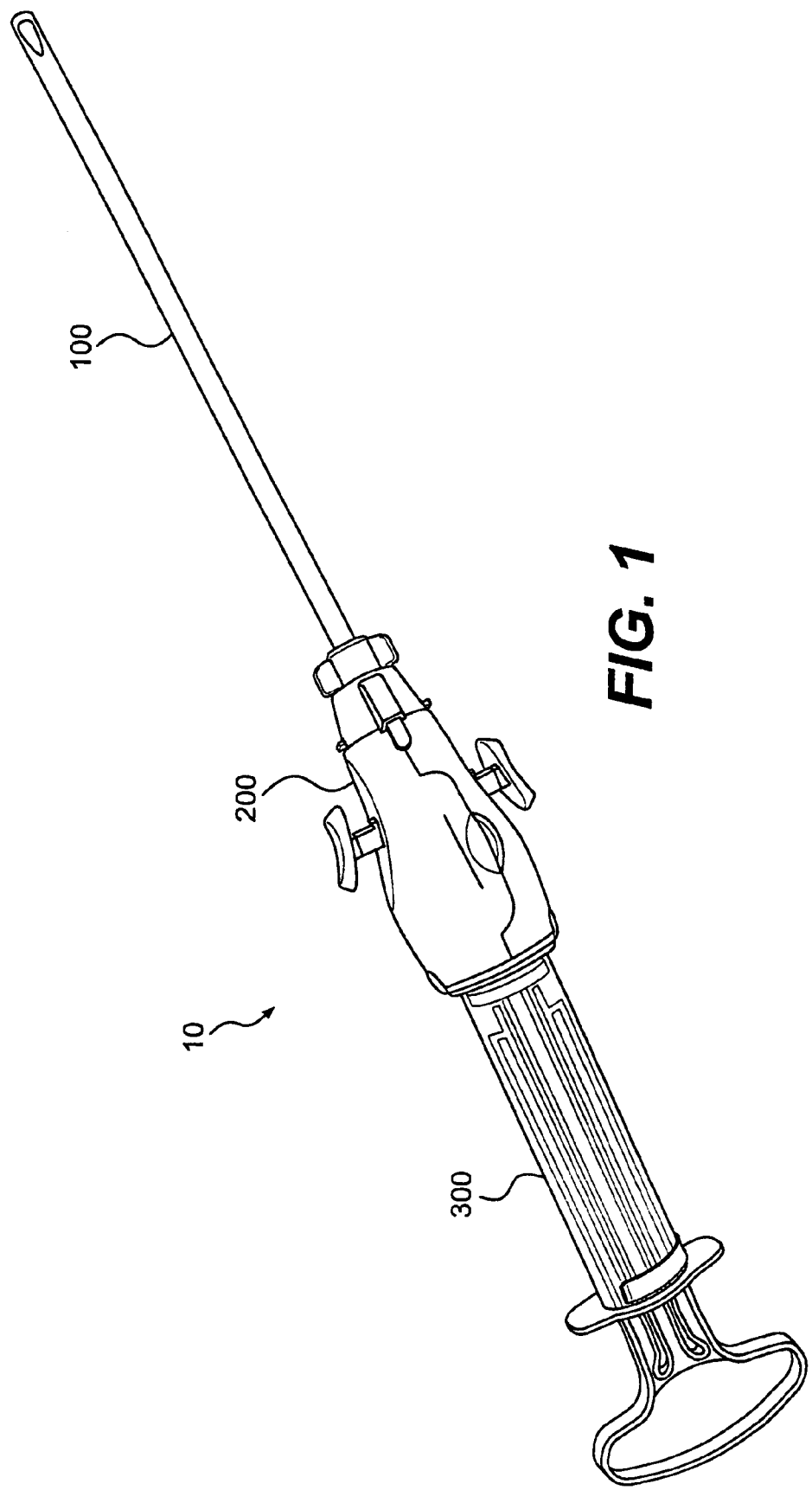
FIG. 1 is a perspective view of an exemplary embodiment of an medical vacuum aspiration device according to the invention.

FIG. 1 illustrates an exemplary embodiment of a medical vacuum aspiration device (MVA) 10. The MVA 10 may include a cannula 100, a valve 200, and an aspirator cylinder 300. The cannula 100 removably connects to a first opening of valve 200 and the aspirator cylinder 300 removably connects to a second opening of the valve 200. The valve 200 opens and closes fluid communication between the cannula 100 and the aspirator cylinder 300.

Figure 3:
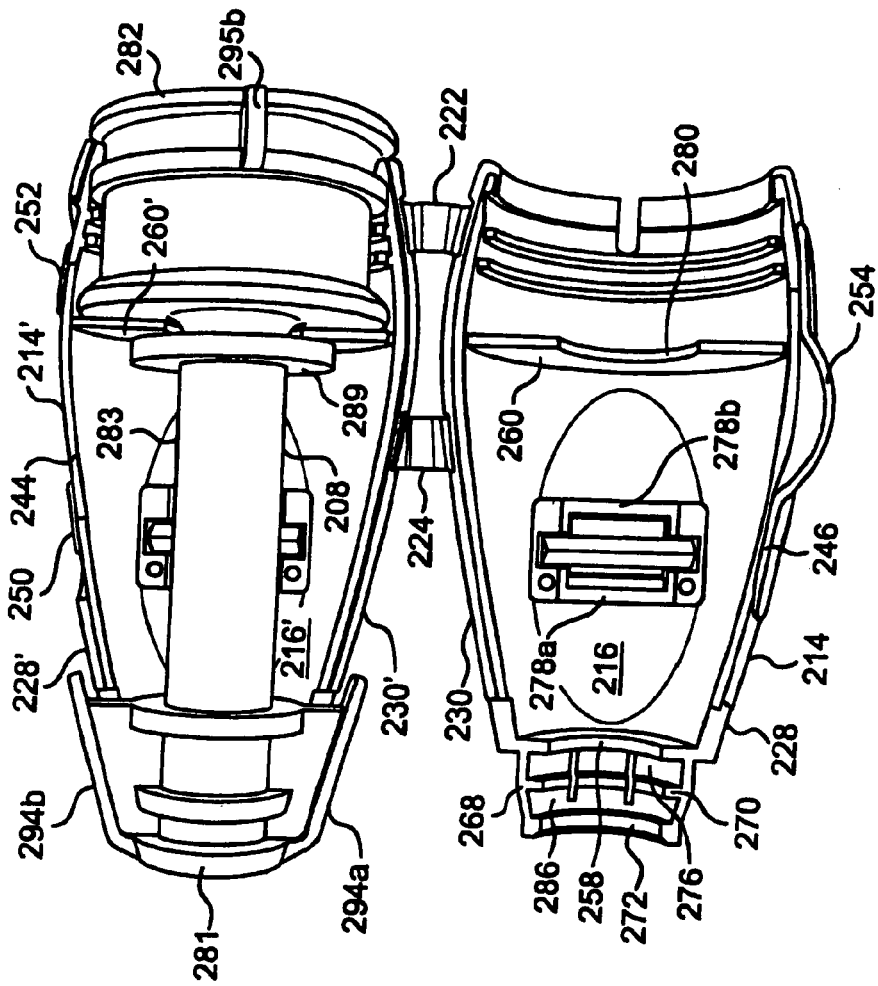
FIG. 3 is a plan view of a housing of the valve according to FIG. 2 with the housing in the opened position and the fluid conduit exposed.
Figure 2:
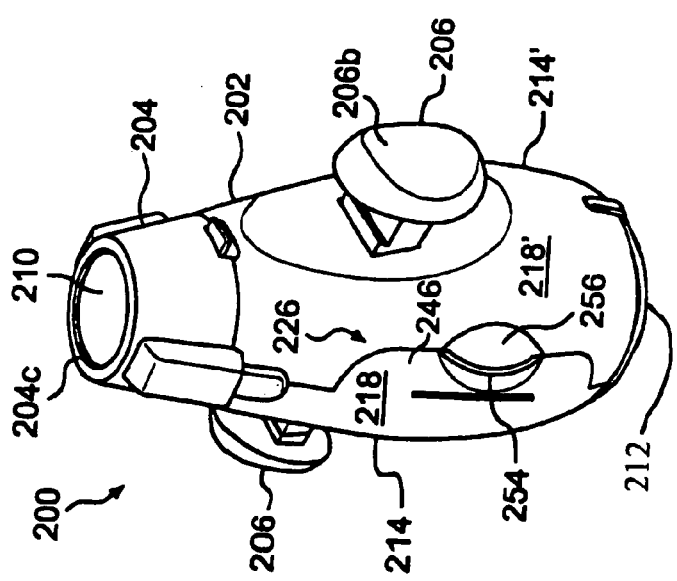
FIG. 2 is perspective view of a valve of the medical vacuum aspiration device according to FIG. 1.

Referring to FIGS. 2 and 3, the valve 200 may include a housing 202, a cap 204, buttons 206, and a fluid conduit 208. The housing 202 includes first and second fluid openings 210, 212 into which the cannula 100 and the aspirator cylinder 300, respectively, are inserted. The housing 202 can be opened to permit access to and removal of the fluid conduit 208. As shown in FIG. 3, an interior of housing 202 receives at least part of the fluid conduit 208. According to one embodiment, each end of the fluid conduit 208 extends outward beyond the respective ends of the housing 202. However, in other embodiments the housing 202 may receive the entirety of the fluid conduit 208. The housing 202 may include alignment and retention features that cooperate with features of the fluid conduit 208 to properly orient and seat the fluid conduit 208 relative to the housing 202. As shown in FIG. 2, the cap 204 may be connected to one end of the housing 202 and can extend over one of the ends of the fluid conduit 208. The cap 204 can be used to reinforce the housing 202 and fluid conduit 208 against deflection that may occur if the cannula is rocked back and forth during use. However, the cap 204 may be omitted from MVAs 10 if such additional reinforcement is not necessary or useful, or is provided by other structural features. Referring to FIG. 1, one end of the fluid conduit 208 can sealingly receive one end of the aspirator cylinder 300 and the other end of the fluid conduit 208 can sealingly receive the cannula 100. However, one or more adapters and/or fluid segments may be provided between the fluid conduit 208 and the cannula 100 and/or the aspirator cylinder 300. Referring to FIG. 2, buttons 206 are movably mounted on the housing 202 to engage and disengage the fluid conduit 208 to close and open, respectively, fluid communication between the cannula 100 and the aspirator cylinder 300, as will be explained later.

Figure 4:
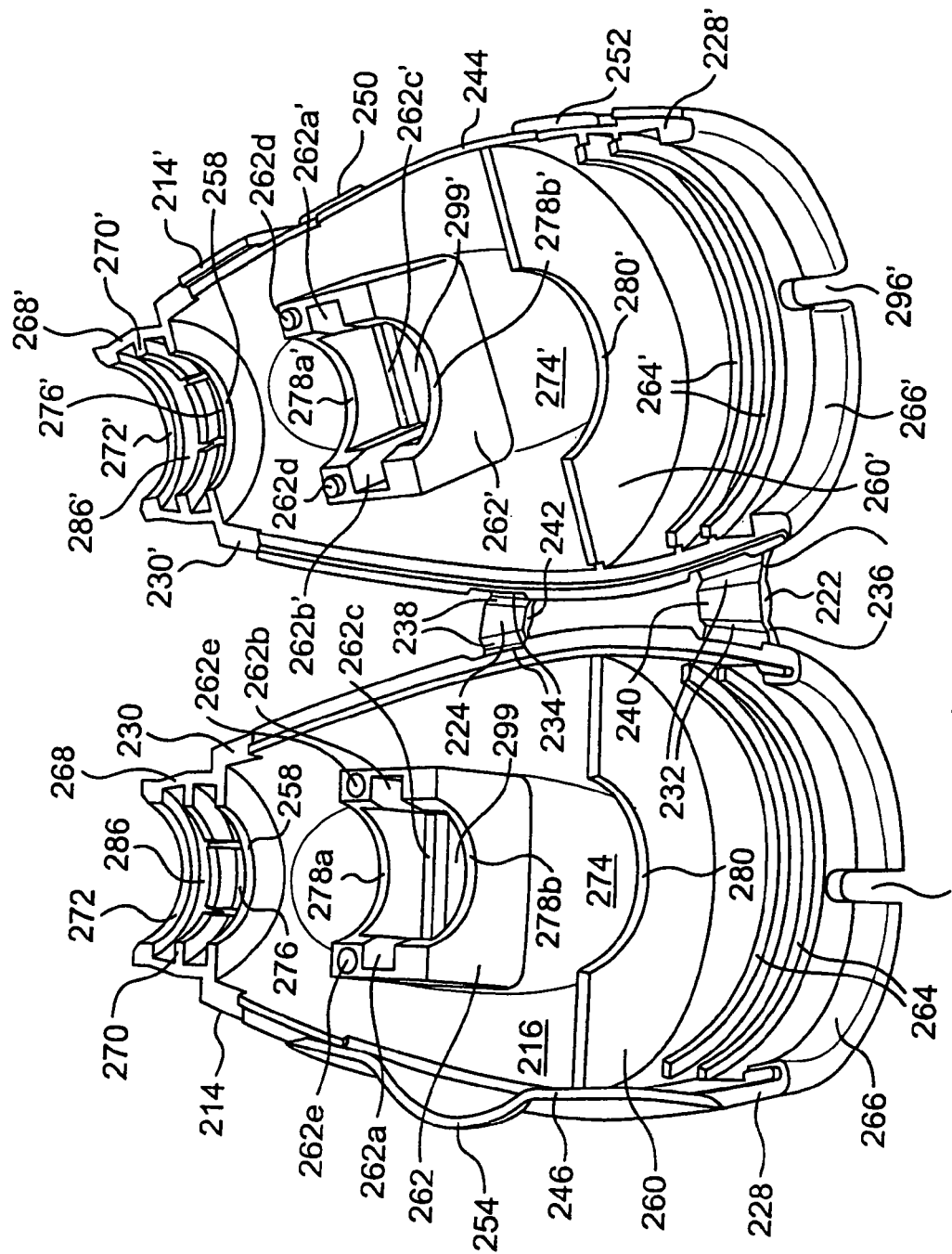
FIG. 4 is a plan view of the inside of the housing according to FIG. 3 with the fluid conduit removed.
Figure 5:
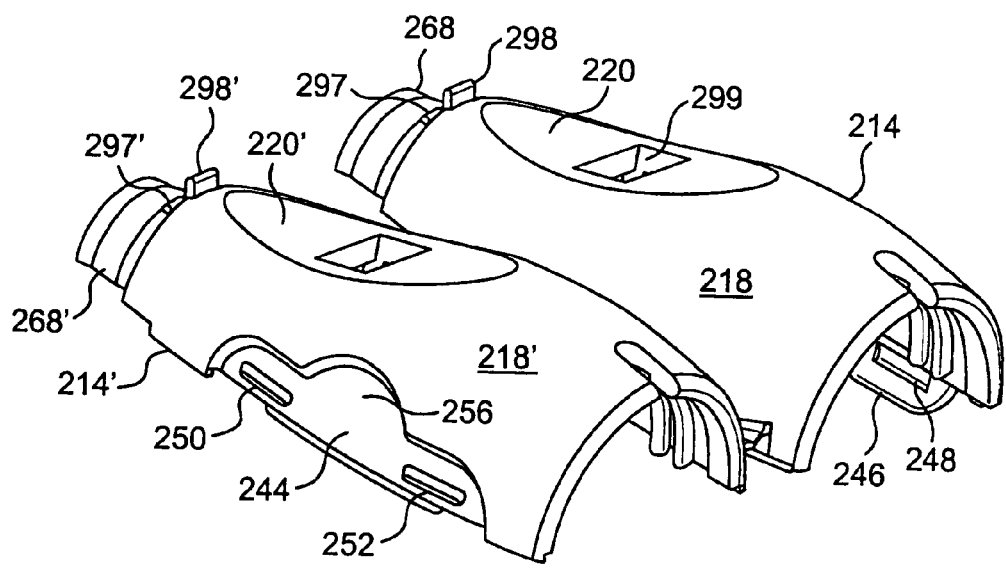
FIG. 5 is a perspective view of the outside of the housing according to FIG. 4.

Referring to FIGS. 2 and 4-6, the housing 202 may include first and second housing walls 214, 214'. The housing walls 214, 214' each include an inner surface 216, 216' and an outer surface 218, 218'. As shown in FIGS. 2 and 3, the inner surfaces 216, 216' cooperate to define a cavity in which the fluid conduit 208 is received and retained. The outer surfaces 218, 218' may cooperate to define an ergonomic shape, such as an ovoid with each end truncated. Of course, the outer surfaces 218, 218' may form other shapes. As shown in FIGS. 3 and 5, the outer surfaces 218, 218' may include concave portions 220, 220'. The concave portions 220, 220' can provide sufficient clearance with the outer surfaces 218, 218' for unobstructed operation of the buttons 206 with ergonomic comfort for the user. As shown in FIGS. 2, 4 and 5, the housing 202 may be generally circular in transverse cross-section, except along the concave portions, and can have a first end that is larger in diameter than a second end. The generally ovoid shape and the concave portions 220, 220' of the outer surfaces 218, 218' of the housing enhance ergonomic comfort for a user's hand.

As note above, the outer surfaces 218, 218' of the housing walls 214, 214' alternatively can be configured to define any desired shape, such as, polygonal, cylindrical, or conical shapes or any combination of such shapes.

Figure 6:
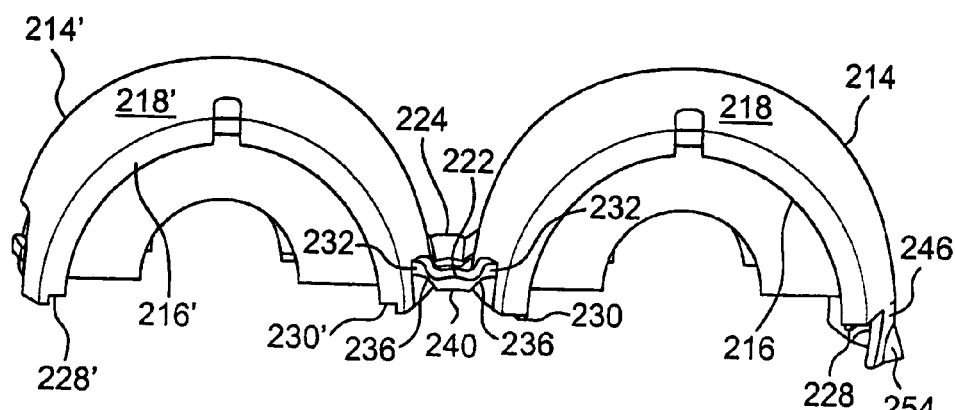
FIG. 6 is an end view of the housing according to FIG. 4.

A releasable connector can permit the housing walls 214, 214' to be joined together to enclose the fluid conduit 208 and taken apart to expose the fluid conduit 208. The housing walls 214, 214' can be releasably connected by hinge straps 222, 224 and a latch 226, as illustrated in FIGS. 4-6, so that the housing walls 214, 214' form a single piece. The hinge straps 222, 224 may connect to the outer surfaces 218, 218' proximate engaging edges 228, 228', 230, 230' of the housing walls 214, 214' by end portions 232, 234 (FIG. 6). The hinge straps 222, 224 enable one housing wall to pivot relative to the other housing wall. Thus, the housing walls 214, 214' can be brought into contact with each other to enclose the fluid conduit 208 (FIG. 2) or opened way from each other to expose the fluid conduit 208 for removal from the valve 200 (FIG. 3) for sterilizing, disinfecting and/or replacement by another fluid conduit 208.

As shown in FIGS. 4 and 6, the hinge straps 222, 224 include living hinge portions 236, 238 spaced inwardly from the end portions 232, 234 and separated by central portions 240, 242. Referring to FIG. 6, the living hinge portions 236, 238 have a reduced thickness as compared to the central portions 240, 242 and end portions 232, 234 to permit one housing wall to pivot relative to the other housing wall. The living hinge portions 236, 238 define double pivot hinges. As shown in FIG. 4, the mating edges 228, 228', 230, 230' of the housing walls 214, 214' are curved from end to end as a result of the general ovoid shape of the housing 202. Preferably, the hinge straps 222, 224 are equidistantly spaced on either side of the apexes of the edges. The double pivot hinges sufficiently space the apexes from each other when the housing walls 214, 214' pivot toward and way from each other such that the apexes do not interfere with the pivoting motion. The double pivot hinges allow the hinge straps 222, 224 to lie adjacent the outer surfaces 218, 218' when the housing 202 is closed and minimize interference with a user's hand. The reduced thickness portions elastically deform and can accommodate repeated bending.

Although two hinge straps are shown, any number of hinge straps can be used as dictated by the shape of the edges of the housing walls. Additionally, other arrangements can be used with or in place of the hinge straps, such as hinge pins or a single living hinge radially spaced from the outer surface by a flange extending from each of the housing walls. While the housing walls have been described as pivoting relative to each other, in the alternative or in addition, other arrangements are also possible that permit rotational and/or translational movement. Also, the housing walls can be releasibly connected together, such as by one or more screws, notches, threads, latches, snaps, pins, clasps, protrusions, indentions, tabs, clips, or other fasteners or combinations thereof, for example, or may be permanently connected by, for example, adhesives, welding or heat staking. Alternatively, the housing could be formed as a continuous one-piece housing that does require further assembly to complete the housing. The fluid conduit can be inserted in the continuous one-piece housing along the longitudinal axis of the housing and the ends of the fluid conduit can be rolled back over the ends of the housing.

Referring to FIGS. 2 and 4-6, the latch includes a tab recess 244 in the outer surface 218' of the second housing wall 214' and a latching tab 246 extending from the edge 228 of the first housing wall 214. Preferably, the tab recess 244 and the latching tab 246 can be located on the outer surfaces 218, 218' of the respective housing portions 214, 214' at a position opposite to the to the positions of the hinge straps 222, 224. In FIG. 5, the latching tab 246 includes recesses 248 (only one is visible) that receive ramps 250, 252 on the tab recess 244 so that the latching tab 248 snaps into engagement with the tab recess 244 to secure the first housing wall 214 to the second housing wall 214'. In one embodiment, the latching tab 246 extends continuously from the outer surface 218 of the first housing wall 214 and lies substantially flush with the outer surface 218' of the second housing wall 214', as illustrated in FIGS. 2 and 6. In FIG. 2, the latching tab 246 includes a partial dome portion 254 that cooperates with a semicircular extension 256 (FIGS. 2 and 5) of the recess 244 to define a space for receiving a user's finger so that the user can disengage the latching tab 246 from the recess 244 and open the housing walls 214, 214'.

In one embodiment, the latch 226, hinge straps 222, 224 and housing walls 214, 214' are integrally coupled to form as a single component. For example, the latch 226, hinge straps 222, 224 and housing walls 214, 214' may be injection molded from a plastic material that can withstand repeated sterilizing/disinfecting procedures (e.g., autoclaving and chemical disinfectants), such as polypropylene, or polymethyl pentene blended with polypropylene. In one embodiment, the housing is made from polypropylene. Alternatively, the hinge straps and the latch could be formed separately from the housing walls and then mounted to the housing walls and other suitable materials such as, polysulfones (e.g., polyphenylsulfone and polyethersulfone), polyethermide, or polymethyl pentene, can be used for the housing and its features.

Referring to FIG. 4, the housing walls 214, 214' may include first conduit support walls 258, 258', second conduit support walls 260, 260', button extensions 262, 262', second conduit support ribs 264, 264', and second lips 266, 266' extending from and along the inner surfaces 216, 216'. Arcuate walls 268, 268' may extend longitudinally from the first conduit support walls 258, 258' and include first conduit support ribs 270, 270' and first lips 272, 272'. The first and second conduit support walls 258, 258', 260, 260', button extension 262, 262', the arcuate walls 268, 268', the first and second conduit support ribs 270, 270', 264, 264', and the first and second lips 272, 272', 266, 266' may be integrally formed on the housing walls by plastic injection molding.

The conduit support walls 258, 258', 260, 260' may lie intermediate the respective first and second support ribs 270, 270', 264, 264'. The button extensions 262, 262' can be located intermediate the first conduit support walls 258, 258' and the second conduit support walls 260, 260'. The inner surfaces 216, 216' may include convex portions 274, 274' aligned with the respective concave portions 220, 220'. In FIG. 4, the button extensions 262, 262' are shown to lie on the convex portions 274, 274'. The conduit support walls 258, 258', 260, 260' and the button extensions 262, 262' can include arcuate recesses 276, 276' 278a, 278a', 278b, 278b', 280, 280'that receive, support and coaxially align the fluid conduit 208 within the housing 202. The conduit support ribs 270, 270, 264, 264' the conduit support walls 258, 258', 260, 260' and the button extensions 262, 262' can cooperate to engage, position and support the fluid conduit 208 inside the cavity of the housing 202.

Figure 7:
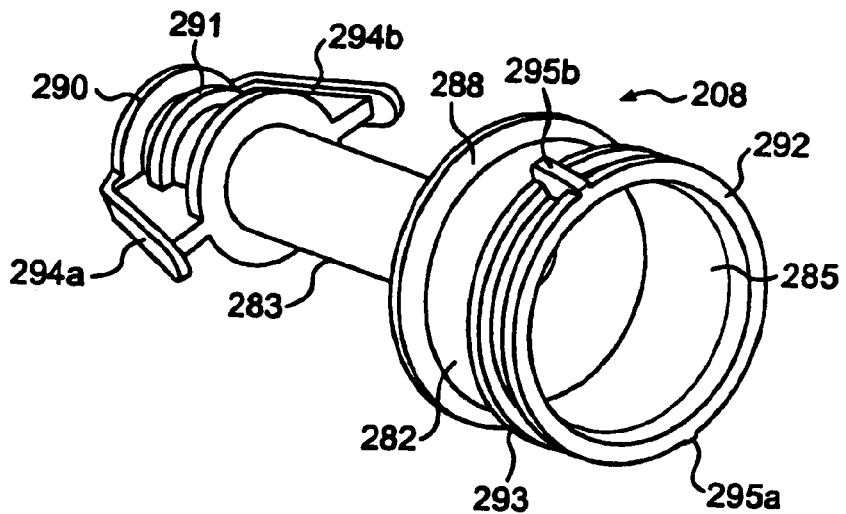
FIGS. 7 and 8 are perspective views of the fluid conduit according to FIG. 3.
Figure 8:
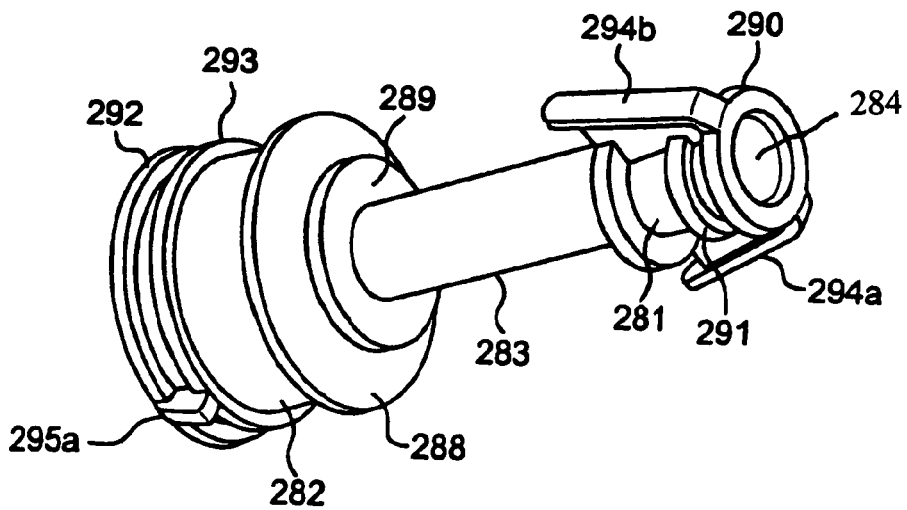

Referring to FIG. 7, the fluid conduit 208 can include a first mounting portion 281, a second mounting portion 282 and a conduit portion 283 connected between and in fluid communication with the first and second mounting portions 281, 282. As shown in FIGS. 7 and 8, the first and second mounting portions 281, 282 include first and second receptacles 284, 285. According to one embodiment, the cannula 100 may be inserted into the first receptacle 284 in a fluid tight manner and the aspiration cylinder 300 may be inserted into the second receptacle 285 in a fluid tight manner. The first mounting portion 281 and the conduit portion 283 include fluid passages in fluid communication with each other and in fluid communication with the respective first and second receptacles 284, 285. The first and second mounting portions 281, 282 and the conduit portion 283 can be cylindrical and coaxially aligned, with the outer diameter of the second mounting portion 282 being greater than the outer diameter of the conduit portion 283 and the first mounting portion 281.

Referring to FIGS. 3 and 4, the inner 286, 286' surfaces of the arcuate walls 268, 268'define a space that can receive the first mounting portion 281 and the inner surfaces 216, 216' of the housing walls 214, 214' define a space at the second end of the housing 202 for receiving the second mounting portion 282. The inner surfaces 286, 286' of the arcuate walls 268, 268' and the inner surfaces 216, 216' of the housing walls 214, 214' at the second end of the housing 202 may be complimentary in size and shape to the first and second mounting portions 281, 282.

As shown in FIG. 7, the first mounting portion 281 can include a first circular flange 287, the second mounting portion 282 can include a second circular flange 288, and the conduit portion 283 can include a third circular flange 289 (FIG. 4). The first circular flange 287 can be located at the junction of the first mounting portion 281 and the conduit portion 283, the second circular flange 288 can be located at the junction of the second mounting portion 282 and the conduit portion 283, and the third circular flange 289 can be located intermediate the first and second circular flanges 287, 288 and closer to the second circular flange 288 than to the first circular flange 287. The first mounting portion 281 can include a first ring 290 at the first end of the fluid conduit 208 and an intermediate ring 291 between the first ring 290 and the first circular flange 287. The second mounting portion 282 can include second ring 292 at the second end of the fluid conduit 208 and third ring 293 spaced inwardly from the second ring 292. The first ring 290 cooperates with the inner surfaces 286, 286' and the lips 272, 272' of the arcuate walls 268, 268' to provide a conforming fit between the housing 202 and the fluid conduit 208 that can accommodate different sizes of cannulae. The ribs 270, 270' can enhance the moldability of the arcuate walls 268, 268' by reducing the cross-sectional area of the arcuate walls 268, 268'. This reduction in cross-section area can reduce the occurrence of sinks and dimensional variation which can adversely affect the aesthetics and/or the vacuum seal. The rings 292, 293 cooperate with the inner surfaces 216, 216' and the lips 266, 266' of the housing walls 214, 214' to provide a conforming fit between the housing 202 and the fluid conduit 208 that can promote the vacuum seal between the valve 200 and the aspirator cylinder 300. Alternatively, separate sealing devices, such as O-rings, can be affixed to one or both of the aspirator cylinder 300 and the fluid conduit to form a fluid tight seal between the aspirator cylinder 300 and the fluid conduit, as will be explained below.

Referring to FIG. 3, the fluid conduit 208 can be mounted in the housing 202 with the first mounting portion 281 located adjacent the first ends of the housing walls 214, 214' and the second mounting portion 282 located adjacent the second ends of the housing walls 214, 214'. The fluid conduit 208 can be received in the housing walls 214, 214' so that the first circular flange 287 lies adjacent the inner faces of the first conduit support walls 258, 258' and the second conduit support walls 260, 260' are sandwiched between the second and third circular flanges 288, 289. The circular flanges 287, 288, 289 cooperate with the conduit support walls 258, 258', 260, 260' to locate the fluid conduit 208 longitudinally within the housing 202. The arcuate recesses 276, 276' 278a, 278a', 278b', 278b', 280, 280' in the conduit support walls 258, 258', 260, 260' and the button extensions 262, 262' may be designed to receive and support the conduit portion 283 and center the conduit portion 283 coaxially about the longitudinal axis of the housing walls 214, 214'. The second support ribs 264, 264' can receive and support the second mounting portion 282 at a position intermediate the third ring 293 and the second circular flange 288.

The fluid conduit 208 can include first radial flanges 294a, 294b extending from the first mounting portion and second radial flanges 295a, 295b extending from the second mounting portion 282. For example, as shown in FIG. 8, the first radial flanges 294a, 294b may be diametrically opposed to each other and the second radial flanges 295a, 295b may be diametrically opposed and spaced at an angle (e.g., ninety degrees) about the longitudinal axis of the fluid conduit relative to the first radial flanges. Referring to FIG. 7, the first radial flanges 294a, 294b extend longitudinally from the first ring 290 to the first circular flange 287 and the second radial flanges 295a, 295b extend longitudinally from the second ring 292 to the third ring 293. Referring to FIGS. 3-5, the edges of the arcuate walls 268, 268' can be spaced from each other to define longitudinal openings extending inwardly from the first end of the housing 202 when the housing walls 214, 214' are closed. The first longitudinal openings receive the first radial flanges 294a, 294b. The second end of the housing 202 can include second longitudinal openings 296, 296' spaced apart (e.g., ninety degrees) about the longitudinal axis of the housing walls 214, 214' relative to the first longitudinal openings. The second longitudinal openings 296, 296' can receive the first and second radial flanges 295a, 295b, respectively. The radial flanges can cooperate with the longitudinal openings to rotationally retain the fluid conduit within the housing 202 during insertion of the cannula 100 and the aspiration cylinder 300. Although one embodiment can have two pairs of radial flanges and longitudinal openings, any number of flanges and openings can be used. Also, other features such as interlocking gear features can be used instead of the flanges and longitudinal openings to reduce rotation of the fluid conduit.

The fluid conduit 208 shown in FIGS. 3, 7 and 8 may be integrally formed as a single component having a continuous fluid passage therethrough. The single component fluid conduit 208 can be made from any suitable resilient material, such as silicone, that can withstand repeated sterilizing by autoclaving and/or chemical treatment.

Referring to FIG. 9, the cap 204 can be removably connected to the housing 202 over the arcuate walls 268, 268' and the first mounting portion 281. The cap 204 can cooperate with the arcuate walls 268, 268' and the latch 226 to retain the housing walls 214, 214' in the closed position (FIG. 2). The cap 204 may encircle both arcuate walls 268, 268' and can resist separation of the housing walls 214, 214' at the first end of the housing 202 that can be caused by movement of the cannula 100 during use of the medical vacuum aspiration device 10.

The cap 204 may include first and second ends, inner and outer surfaces (e.g., having generally frustoconical shapes), and arms 204a extending outwardly from the outer surface. The inner surface of the cap 204 may be complimentary in size and shape to the arcuate walls 268, 268' and defines a cavity that can receive the first mounting portion 281. The arms 204a include channels 204b that open to the inner surface of the cap 204 and can receive the first radial flanges 294a, 294b of the fluid conduit 208. The arms 204a can cooperate with the first radial flanges 294a, 294b to restrain rotational displacement of the first mounting portion 281 relative to the housing 202 during insertion of the cannula 100 into the first mounting portion 281.

As shown in FIG. 2, the first end of the cap 204 can include a rounded lip 204c. The first ring 290 can be located between and engaged by the rounded lip 204c and the ends of the arcuate walls 268, 268'. The rounded lip 204c at least partially overlaps the first ring 290.

The cap 204 includes features for removably connecting the cap 204 to the housing walls 216, 216'. For example, the inner surface of the cap 204 can include a circumferential groove 204d extending between the channels 204b proximate the second end of the cap 204. The circumferential groove 204d can receive ramps 297, 297' (FIG. 5) extending from the outer surfaces of the arcuate walls 268, 268'. The groove 204d can cooperate with the ramps 297, 297' to provide a snap fit between the cap 204 and the arcuate walls 268, 268' so that the cap 204 can be removably connected to the housing walls 214, 214'. The second end of the cap 204 can include diametrically opposed recess 204e that can receive diametrically opposed tabs 298, 298'(FIG. 5) extending radially from the outer surface of the arcuate walls 268, 268'. The recesses 204e can cooperate with the tabs 298, 298' to reduce rotation of the cap 204 relative to the housing 202.

Referring to FIGS. 3 and 5, the housing walls 214, 214' can include button openings 299, 299' through which the buttons 206 extend into the housing 202 and can engage the fluid conduit 208. Preferably, the button extensions 262, 262' can include a plurality of recesses 262a, 262a', 262b, 262b', 262c, 262c' that each extend from the end faces of the button extensions 262, 262'to the inside surface 216, 216' of the housing walls 214, 214'. As will be explained below, these recesses 262a, 262a', 262b, 262b', 262c, 262c' can cooperate with the buttons 206 to locate, guide and restrain the buttons 206 within the housing 202. Pins 262d can extend from button extension 262' of the second housing wall 2124' and engage blind holes 262e in the button extension 262 of the first housing wall 214 when the housing walls 214, 214' are closed together. The pins 262d can cooperate with the blind holes 262e to ensure proper alignment of the button extensions 262, 262' when the housing walls 214, 214' are closed.

Referring to FIGS. 10 and 11, the buttons 206 can include a button face 206a (FIG. 10) and a clamp stem 206b (FIG. 11). As shown in FIGS. 2 and 10, the button face 206a can provide an interface for receiving a user's finger to effect opening and closing of the valve 200. The button face 206a is positioned external to the housing 202 for actuation by a user can so that the valve 200 can be selectively opened and closed. The button face 206a can be oval in shape and can include a concave contact surface for engagement by a user's finger. Alternatively, other shapes for the button face 206a can be used, such as rectangular, convex, and planar. Preferably, the button faces 206a can be separate components from the respective clamp stems 206b and can be made larger than the button openings 299, 299' to prevent displacement of the button faces 206a through the button openings 299, 299' and into the housing 202. The button faces 206a can be connected to one end the respective clamp stems 206b by any conventional fastening methods, such as welding, adhesives or fasteners. A post 206c may extend from the bottoms of the button faces 206a and be received in respective blind holes 206d formed in the clamp stems 206b, as shown in FIG. 11.

To assemble the buttons 206 in the housing walls 214, 214', preferably, the button faces 206a are properly oriented over the button openings 299, 299' above the outer surface 218, 218'of the housing walls 214, 214' and the clamp stems 206b are aligned over the button openings 299, 299' above the inner surfaces 216, 216' of the housing walls 214, 214'. The clamping stems 206b can be passed through the button openings 299, 299' and the posts 206c can be inserted to the blind holes 206d. The button faces 206a and the clamp stems 206b can be secured together, for example, by adhesives or welding.

The clamp stems 206b can extend through the respective button openings 299, 299' in housing walls 214, 214' and slide along the respective button extensions 262, 262' between a valve closed position and a valve opened position. The button openings 299, 299' and the cross-sections of the clamp stems 206b can be rectangular in shape. However, other shapes can be used for the button openings and the clamp stems, such as, oval, triangular, pentagonal, cruciform, etc.

Referring to FIG. 11, a conduit clamp 206e can be connected to the other end of the clamp stem 206b. The conduit clamp 206e may include a wedge-shaped transverse cross-section. The conduit portion 283 of the fluid conduit 208 includes a resilient portion that is engaged by the conduit clamps 206e. The conduit clamps 206e are biased to an opened position by the resilient portion of the conduit portion 283 and movable by a user pushing the button faces 206a toward the resilient portion against the bias of the resilient portion to move the conduit clamps 206e to a closed position. The recesses 262a, 262a', 262b, 262b' receive and guide the ends of the conduit clamps 206e as the clamps 206e move between the closed and opened positions. The button mechanism can be designed to provide either a normally open valve 200 or a normally closed valve 200.

Preferably the clamp stems 206b and the conduit clamps 206e are integrally formed from any material that can withstand repeated sterilizing by autoclaving and/or chemical disinfecting. The button faces 206a, clamp stems 206b and conduit clamps 206e can be formed from any suitable a material that can withstand repeated conventional sterilizing and cleaning procedures (e.g., autoclaving and chemical disinfectants), such as polyethermide, polyoxyethylene copolymer, polysulfones (e.g., polyphenylsulfone and polyethersulfone), polyethermide, and polymethyl pentene. In the preferred embodiment, the button faces 206a, the clamp stems 206b and the conduit claims 206e are made from polyethermide or polyoxyethylene. The conduit clamps 206e can have ends that extend transversely beyond the transverse width of the openings 299, 299'. The ends can have stop faces 206f that engage the inner surface 216, 216' of the housing walls 214, 214' in the recesses 262a, 262a', 262b, 262b' and can prevent removal of the buttons 206 by displacing the buttons 206 outwardly of the housing 202. The stop faces 206f can cooperate with inner surface 216, 216' and bottoms of the button faces 206a can cooperate with the outer surfaces 218, 218' of the housing walls 214, 214' to retain the buttons 206 in the button openings 206 when the housing is closed or opened.

To close the valve 200, a user pushes on the buttons 206 inwardly toward the housing 202 to move the conduit clamps 206e to compress the resilient portion of the conduit portion 283 against the bias of the resilient portion and collapse the fluid passage of the conduit portion 283. The valve 200 is in the closed position when the fluid passage is collapsed. Preferably, the buttons 206 can be diametrically opposed and the conduit clamps 206e clamp the resilient portion between them.

The buttons 206 may be set to lock the valve 200 in a closed position. For example, a locking projection 206g can extend away from the stem 206b and engage a respective recess 262c, 262c' in the button extensions 262, 262' to maintain the buttons 206 in the valve closed position against the bias of the resilient portion of the conduit portion 283. After the buttons 206 have been moved to the valve closed position, the user may push the buttons 206 longitudinally toward the first end of the housing 202 until the locking projections 206g extend fully into the recesses 262c, 262c'. The bias of the resilient portion of the conduit portion 283 pushes the projections 206g into engagement with the inner surface 216, 216' of the housing wall 214, 214'and can hold the buttons 206 in the valve closed position. In order to release the buttons 206 from the valve closed position and return the buttons 206 to the valve opened position, the user may pull the buttons 206 toward the second end of the housing 202 to disengage the locking projections 206g from the recesses 262c, 262c'. The bias of the resilient portion of the conduit portion 283 pushes the buttons 206 outward from the conduit portion 283, returns the buttons 206 to the valve opened position, and opens the fluid passageway of the conduit portion 283.

Although an embodiment in which two buttons collapse the fluid passageway is described above, it should be understood that a single button can be used to collapse the fluid passageway. Alternatively, the buttons can include pivoting links, gears, springs or combinations thereof.

In the embodiment illustrated in FIGS. 1 and 12, the aspiration cylinder 300 is in the form of a syringe 302. Alternatively, the aspiration cylinder 300 can be any one of a variety of components in which a vacuum can be drawn, such as, an electric vacuum pump or a type of manual vacuum pump manual that is different from the aspiration cylinder 300. The syringe 302 can include a collection tube 304, a plunger 306 slidably received in the collection tube and a handle 308 connected to the plunger 306.

Referring to FIGS. 12 and 13, the collection tube 304 may cylindrical and can include two open ends. A first end 322 of the collection tube 304 can be inserted into the second end of the housing 200 to engage the base of the second receptacle 285 of the fluid conduit. The base of the receptacle and the first end 322 of the collection tube 304 cooperate to form a vacuum seal therebetween. An elongate flange 312 can be mounted at one end of the collection tube 304. The elongate flange 312 can provide a grip for a user when the handle 308 is displaced by the user. Mounting rings 314, 316 can be located proximate the other end of the collection tube 304. The mounting rings 314, 316 can reduce the surface area of the collection tube 304 that contacts the second receptacle 285 during insertion and removal of the tube 304, thereby, reducing the insertion and removal forces. The mounting rings 314, 316 can cooperate with the inner surface of the second receptacle 285 in the second mounting portion 282 of the fluid conduit 208 to provide a secondary vacuum seal between the valve 200 and the collection tube 302.

Referring to FIG. 12, the plunger 306 can include an O-ring 310 that cooperates with the inner surface of the collection tube 304 to form a fluid seal between the plunger 306 and the collection tube 304. Alternatively, a plunger tip such as that commonly used on smaller syringes could be used in place of the O-ring.

Referring to FIGS. 12 and 14, a plunger stop 318 can be connected to the collection tube 304 proximate the elongate flange 312. The plunger stop 318 can include an arcuate body having two free ends and two projections 324 (FIG. 14). The projections 324 can extend from the arcuate body proximate the free ends and can pass through respective holes 326 (FIG. 13) in the side of the collection tube 304. Preferably, the plunger 306 contacts the projections 324 to prevent removal of the plunger 306 from inside the collection tube 304. When the valve 200 is closed, a vacuum can be drawn in the collection tube 304 by displacing the plunger 306 toward the flange 312. The valve 200 may then be opened to create suction at the end of the cannula 100. A retaining clip 328 can extend from the elongate flange 312 and over the plunger stop 318. The retaining clip can hold the plunger stop on the collection tube 304 when the projections 324 are removed from the holes 326. The retainer clip 328 and the flange 312 can be integrally formed.

As shown in FIGS. 12 and 13, the plunger 306 can include lock faces 330 that can expand radially outward when the plunger 306 is displaced toward the second end 332 of the tube 304 and engage a rim 334 at the second end 332. The lock faces 330 cooperate with the rim to retain the plunger 306 adjacent the second end 332.

It should be appreciated that other structure for generating a vacuum can be used in connection with the valve 200 described herein. For example, the collection tube 304 may be evacuated with a pump.

Figure 15:
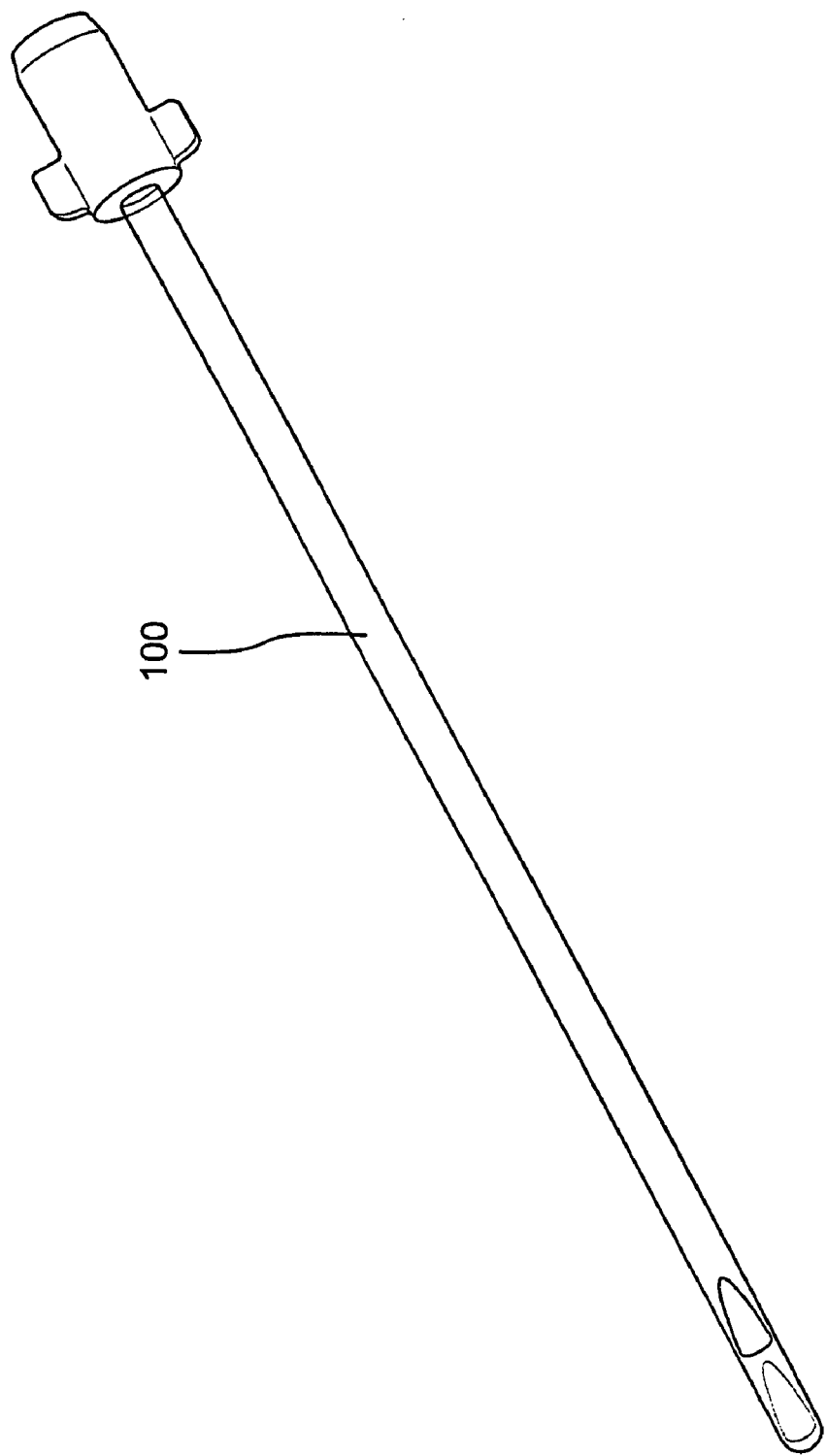
FIG. 15 is a perspective view of the cannula of the medical vacuum aspiration device according to FIG. 1.

FIGS. 1 and 15 illustrate a cannula 100 that is consistent with the invention. it should be understood that other cannula designs can be used.

While the present invention has been disclosed with reference to certain embodiments, numerous modifications, alterations and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What we claim is:

1. A medical vacuum aspiration device comprising:
   an aspiration cylinder;
   a cannula;
   a plunger slidably received in the aspiration cylinder for drawing a vacuum in the aspiration cylinder; and
   a valve, the valve comprising:
      a removable fluid conduit having a first end directly engaging the aspiration cylinder and a second end directly engaging the cannula, said fluid conduit made from a resilient material;
      a valve housing having at least first and second housing portions that define a cavity for removably holding at least a portion of the fluid conduit;
      means for removably attaching the first housing portion to the second housing portion; and
      an actuator, coupled to the valve housing, that selectively compresses a portion of the fluid conduit to open and close a fluid path defined by the fluid conduit;
   wherein the fluid conduit further comprises a first receptacle proximate the first end, the first receptacle receiving an end of the aspiration cylinder to provide a sealed connection between the fluid conduit and the aspiration cylinder.

2. The medical vacuum aspiration device according to claim 1, wherein the first and second housing portions and the means for removably attaching comprise a single-piece unit.

3. The medical vacuum aspiration device according to claim 2, wherein the single-piece unit comprises plastic.

4. The medical vacuum aspiration device according to claim 3, wherein the plastic comprises polypropylene.

5. The medical vacuum aspiration device according to claim 1, wherein the fluid conduit and the first receptacle comprises an integrally formed conduit component such that the fluid passageway extends continuously through the fluid conduit.

6. The medical vacuum aspiration device according to claim 1, wherein the resilient material comprises silicone.

7. The medical vacuum aspiration device according to claim 1, wherein the first and second housing portions engage the fluid conduit to restrain movement of the fluid conduit relative to the housing.

8. The medical vacuum aspiration device according to claim 7, the valve further comprising a cap that connects to the first and second housing portions.

9. The medical vacuum aspiration device according to claim 8, wherein a portion of the fluid conduit extends outwardly from an end of the housing and the cap extends over the portion of the fluid conduit.

10. The medical vacuum aspiration device according to claim 9, wherein the cap engages the fluid conduit to restrain movement of the fluid conduit relative to the housing.

11. The medical vacuum aspiration device according to claim 1, wherein the first receptacle is integrally formed portion of the fluid conduit.

12. A medical vacuum aspiration device comprising:
   an aspiration cylinder;
   a plunger slidably received in the aspiration cylinder for drawing a vacuum in the aspiration cylinder;
   a cannula and
   a valve adapted for fluid communication with the aspiration cylinder, the valve including:
      first and second housing portions, each including inner and outer walls;
      a releasable connector joining the first housing portion to the second housing portion such that the first housing portion and the second housing cooperate to define a housing having first and second open ends and a cavity defined by the inner walls and extending between the first and second open ends;
      a flexible fluid conduit retained in the cavity when the first and second housing portions are joined by the releasable connector, and the fluid conduit exposed for removal from the cavity when the releasable connector is released, the flexible fluid conduit including a first end directly engaging the aspiration cylinder, a second end directly engaging the cannula, and a flexible conduit clamping portion; and
      at least one conduit clamp movably mounted on one of the housing portions and engagable with the flexible conduit clamping portion to compress the conduit clamping portion;
   wherein the fluid conduit further comprises a first receptacle proximate the first end, the first receptacle receiving an end of the aspiration cylinder to provide a sealed connection between the fluid conduit and the aspiration cylinder; and
   the fluid conduit further comprises a second receptacle proximate the second end, the second receptacle receiving an end of the cannula to provide a sealed connection between the fluid conduit and the cannula.

13. The medical vacuum aspiration device according to claim 12, further comprising a hinge about which the first housing portion pivots relative to the second housing portion.

14. The medical vacuum aspiration device according to claim 13, wherein the hinge comprises a living hinge.

15. The medical vacuum aspiration device according to claim 14, wherein the hinge comprises two living hinges integrally formed on the housing portions.

16. The medical vacuum aspiration device according to claim 15, wherein each of the living hinges comprises a double living hinge.

17. The medical vacuum aspiration device according to claim 13, wherein the releasable connector comprises a releasable latch.

18. The medical vacuum aspiration device according to claim 17, wherein the releasable latch comprises a latch tab extending from an edge of one of the housing portions and a tab recess in an outer surface of another one of the housing portions, the tab recess releasably receiving the latch tab when the releasable connector joins the housing portions.

19. The medical vacuum aspiration device according to claim 18, wherein the latch tab further comprises a dome portion cooperating with the tab recess to define a user interface space.

20. The medical vacuum aspiration device according to claim 19, wherein the latch tab and tab recess are integrally formed on a respective one of the housing portions.

21. The medical vacuum aspiration device according to claim 12, wherein the valve further comprising a cap connected to at least one of the first and second ends of the housing.

* * * * *